(12) United States Patent
Ahumada Ayala et al.

(10) Patent No.: US 8,349,889 B2
(45) Date of Patent: Jan. 8, 2013

(54) SKIN-CARE PREPARATIONS CONTAINING MUPIROCIN AND BETAMETHASONE DIPROPIONATE

(75) Inventors: Fernando Ahumada Ayala, Colonia Tlalpan (MX); Francisco Javier Padilla-Gomez, Cuicuilco (MX)

(73) Assignee: Laboratorios Dermatologicos Darier, S.A. DE C.V., Col. Tlalpan Centro (MX)

( * ) Notice: Subject to any disclaimer, the term of this patent is extended or adjusted under 35 U.S.C. 154(b) by 602 days.

(21) Appl. No.: 12/065,352

(22) PCT Filed: Sep. 28, 2005

(86) PCT No.: PCT/MX2005/000084
§ 371 (c)(1),
(2), (4) Date: Mar. 18, 2009

(87) PCT Pub. No.: WO2007/027077
PCT Pub. Date: Mar. 8, 2007

(65) Prior Publication Data
US 2010/0063015 A1    Mar. 11, 2010

(30) Foreign Application Priority Data
Sep. 2, 2005    (MX) .................... PA/a/2005/009381

(51) Int. Cl.
*A01N 43/16*    (2006.01)
*A61K 31/35*    (2006.01)
*A01N 35/00*    (2006.01)
*A61K 31/12*    (2006.01)

(52) U.S. Cl. ...................................... 514/460; 514/690

(58) Field of Classification Search ................... 514/460, 514/690
See application file for complete search history.

(56) References Cited

U.S. PATENT DOCUMENTS

| | | | | |
|---|---|---|---|---|
| 6,013,657 | A | 1/2000 | Lavon et al. | 514/330 |
| 6,451,339 | B2 * | 9/2002 | Patel et al. | 424/451 |
| 2002/0111336 | A1 | 8/2002 | Hoy et al. | 514/167 |

FOREIGN PATENT DOCUMENTS

| | | |
|---|---|---|
| EP | 231621 A1 | 8/1987 |
| EP | 1 174 133 A | 1/2002 |
| EP | 1 932 525 B1 | 11/2010 |

OTHER PUBLICATIONS

Mourya, et al., "Evaluation of mupirocin in mupirocin ointment and mupirocin with betamethasone dipropionate ointment". Eastern Pharmacist, 2000, vol. 43 (505), pp. 143-145.
Savant, et al. *Journal of the Indian Medical Association*, 98(4): 194-195 (Apr. 2000). Abstract.
Claims, Response, Opinion, and Supplementary EP Search Report for EP 1932525B1.

* cited by examiner

*Primary Examiner* — Benjamin Packard
(74) *Attorney, Agent, or Firm* — Dara L. Dinner; Theodore R. Furman

(57) ABSTRACT

The present invention relates to a topical skin-care preparation in the form of an ointment containing mupirocin and betamethasone dipropionate as active principles and a carrier formulated with all or some of the following components: hydrogenated castor oil, polyethylene glycols and preservatives. The inventive preparation is advantageous over prior art compositions in that it has a specific therapeutic effect on primary and secondary skin infections, such as relief of pruritic inflammatory manifestations of dermatosis, a wide range of activity against the majority of bacterial species involved in skin infections, and a high level of activity against *Staphylococcus* and *Streptococcus*, including multi-resistant strains. In addition, the therapeutic effect of the preparation is not affected by the size of the inoculum and the preparation has no sensitization potential, thereby providing the product with an excellent safety profile for use by the patient. Moreover, the preparation can counteract the possible secondary effects of one of the components with the effect of another.

7 Claims, No Drawings

SKIN-CARE PREPARATIONS CONTAINING MUPIROCIN AND BETAMETHASONE DIPROPIONATE

This application is a national stage application of co-pending PCT application PCT/MX2005/000084 filed Sep. 28, 2005, which was published in Spanish under PCT Article 21(2) on Mar. 8, 2007, which is incorporated by reference herein in its entirety.

FIELD OF THE INVENTION

The present invention relates to a topical skin-care preparation in the form of an ointment containing mupirocin and betamethasone dipropionate as active principles and a carrier formulated with all or some of the following components: hydrogenated castor oil, polyethylene glycols and preservatives.

BACKGROUND OF THE INVENTION

The therapeutic applications of the product to be patented, taking into account the combination of both active principles, are the following:

In primary and secondary skin infections, such as:
a) Impetigo
b) Hypoderma
c) Cellulitis
d) Balanitis
e) Folliculitis
f) Furunculosis
g) Styme
h) Abrasions
i) Infected burnings
j) Infected psoriases
k) Infected ulcers For the relief of inflammatory manifestations of hyperkeratosic dermatoses and dry dermatoses which respond to corticosteroids such as psoriasis, chronic atopic dermatitis, neurodermatitis (chronic simple lichen), lichen planus, eczema (including nummular eczema, hand eczema, dermatitis eczematosa), dyshidrosis (pompholyx), scalp seborrheic dermatitis, ichthyosis vulgaris and other ichthyosical affections.

It is possible to find in the state of the art that mupirocin is a broad spectrum antibiotic, obtained by fermentation from *Pseudomonas fluorescens* and that betamethasone dipropionate is a synthetic fluorinated corticosteroid.

Betamethasone dipropionate is a synthetic corticosteroid for dermatological topical use which at pharmacological doses displays anti-inflammatory, antipruritic and vasoconstricting effects. This is due to the lysosomal membrane stabilization, which precludes extracellular release of inflammation mediators. Also betamethasone dipropionate on skin has an inhibition effect on polyamine synthesis, an active component in cell proliferation and growth. It also produces immune system suppression, keratinocyte DNA synthesis inhibition and vasoconstriction. With this, the role of betamethasone dipropionate in the efficiency, efficacy, safety and absorption ability to the action site is demonstrated.

Mupirocin inhibits in vivo synthesis of bacterial proteins, preventing isoleucine (Ile) incorporation to the protein by reversible and specific binding to bacterial isoleucil transfer-RNA synthase (FIG. 4). Due to this action mechanism, mupirocin shows no cross-resistance with other antibiotics such as: chloramphenicol, erythromycin, fusidic acid, gentamycin, lincomycin, methicillin, neomycin, novobiocin, penicillin, streptomycin, and tetracycline.

Mupirocin is an antibacterial agent that inhibits Gram-positive and Gram-negative bacteria growth. Bacteria susceptible to in vitro mupirocin action include aerobic strains of *Staphylococcus aureus* (including methicillin-resistant strains and beta lactamase-producing strains), *Staphylococcus epidermidis*, other staphylococci such as positive or negative α-streptococcus hemolytic coagulase, hemolytic beta streptococcus, *streptococcus* group A (including *S. pyogenes*), other beta *streptococcus* (including *S. agalactiae*), *streptococcus* type D (including *S. faecalis* and *S. faecium*), *streptococcus* group viridians, *Streptococcus pneumoniae, Corynebacterium hofmanil, Bacillus subtilis, Escherichia coli, Klebsiella pneumonia, Proteus mirabilis, Proteus vulgaris, Enterobacter cloacae, Enterobacter aerogenes, Citrobacter freundii, Haemophilus* influenzae (including beta lactamase-producing strains), *Neisseria gonorrheae* (including beta lactamase-producing strains), *Neisseria meiningitidis, Brahamella catarrhalis* and *Pasteurella multocisa*, and anaerobic isolates of *Peptostreotococcus anaerobius, Clostridium difficile* and *Clostridium sporogenes*.

It is also known that PEG 40 hydrogenated castor oil is a fatty acid triglyceride. It is a polyethylene glycol derived from hydrogenated castor oil with an average 40 mol of ethylene oxide.

On other hand, is it widely known that Polyethylene glycol 600 and PEG 150 Distearate are ethylene oxide and water polycondensation products or also known as polyethylenic glycols with molecular weights ranging from 200 to 8000. Only one or a combination of different polyethylene glycols with different molecular weights can be used as main carriers and/or thickeners.

An anti-inflammatory mechanism is at the cell membrane level, acting in two ways: by direct action or through lipocortin which in turn inhibits phospholipase A2, thus blocking arachidonic acid activation and preventing prostaglandin, thromboxane and leukotriene production and hence reducing the anti-inflammatory process.

Corticosteroid specific receptors have been identified on skin both on normal human epidermis and in dermal fibroblasts with which its antiproliferative effect is correlated. Immunosupressing activity of topical corticosteroids is due to these molecules causing a Langerhans cell reduction, inhibiting T cell activity by inducing apoptosis thereof and of eosinophils, as well as blocking the cell cycle.

Savant et al., conducted a study directed to determining the therapeutic efficacy and safety of mupirocin 2%/betamethasone dipropionate 0.05% ointment in the treatment of infected dermatoses. For this, different specialized physicians from different parts of India were invited, who prospectively analyzed the clinical evolution of the patients enrolled in the study for a period of 7 days. The participating patients applied this medicament three times a day both in primary infections complicated by some kind of dermatosis as in those secondarily infected dermatoses. A total of 251 patients and 27 physicians were included in the study; mupirocin 2%/betamethasone dipropionate 0.05% ointment showed a 94.8% efficacy on the infected dermatoses; more than 70% of these patients displayed a clinical improvement after 7 days of initiating the treatment. No adverse effects were reported during treatment. With these data the participant physicians concluded that mupirocin 2%/betamethasone dipropionate 0.05% ointment proved to be a safe and efficient medicament for treating infected dermatoses.

OBJECTS OF THE INVENTION

One of the objects of the present invention is to make possible a medicament having specific therapeutic action against primary and secondary skin infections as well as the relief of dermatoses inflammatory and pruritic manifestations.

Another object is to have a product that assures a broad activity spectrum against the majority of bacterial species involved in skin infections and further having a high level of activity against *staphylococcus* and *streptococcus*, including multi-resistant strains.

Yet another object is to produce a medicament which therapeutic action is not affected by the size of the inoculum, and further having no sensitization potential, thereby providing the product with an excellent safety profile for use by the patient, and further having the ability to counteract the possible secondary effects of one of the components with the effect of another.

Still another object is to confer the active compounds a rapid and more elevated percutaneous absorption or penetration.

Other objects and advantages of the present invention will be apparent from studying the following description and attached drawings, only for illustrative and no limitative purposes.

SUMMARY OF THE INVENTION

Corticosteroid percutaneous absorption is dictated by many factors, such as epidermal barrier integrity, the use of dressings or clothing on the application site, etc. As all topical corticosteroids, percutaneous absorption of betamethasone dipropionate is increased in the skin's inflammatory processes and with the use of occlusive dressings. Once absorbed, said topical corticosteroids display a pharmacokinetic profile similar to that of systemic corticosteroids. They can bind plasma proteins at different concentrations, are primarily metabolized in the liver and are excreted trough kidneys and bile ducts.

The extended use of topical corticosteroids in dermatology is due to their anti-inflammatory, antiproliferative and immunosupressing effects. Steroids are somewhat hydrophobic molecules able to pass through cell membranes by simple diffusion or through specific receptors. The molecular mechanism involved in the anti-inflammatory action starts with its binding to cytoplasm receptors, forming a complex that is dimerized and translocated to the nucleus and which is able to bind DNA, where it binds glucocorticoid response elements, resulting in an increase of the transcription genes which encode anti-inflammatory proteins, such as lipocortin 1, interleukin 10, endopeptidase antagonist and neutral receptor.

The most important effect is at the level of inhibition of the expression of genes related to the production of multiple inflammatory proteins: cytokines, enzymes, adhesion molecules and receptors; this inhibitory effect is due to the interaction of the activated corticosteroid receptor and a transcription factor such as kappa B nuclear factor and protein 1/calpactin activating factor, which regulate the expression of inflammatory genes.

With clinical studies it was demonstrated that mupirocin ointment, C-14-labeled, at the lower part of the arm of healthy male subjects, followed by occlusion for 24 hours, showed no measurable systemic absorption. The measurable radioactivity was limited to the stratum corneum in these subjects 72 hours after its application. Mupirocin ointment showed no late hypersensitivity, contact sensitivity, phototoxicity or photocontact sensitivity, in studies conducted in normal subjects.

Also, in a study performed on 23 healthy subjects it was confirmed that the application of 2% mupirocin ointment on a body surface area of 400 $cm^2$ once a day, reported as added urinary excretion mean corresponding to monic acid 1.25% (0.2% to 3.0%) of the total mupirocin dose applied. The urinary concentration of monic acid taken at specific intervals during 24 hours up to day 7 of the study ranged between <0.050 to 0.637 μg/mL.

After several tests it could be determined that mupirocin has bactericide action at the obtained concentrations in a 2% topical formulation.

An animal model study was performed in order to demonstrate the efficacy of mupirocin when compared to systemic or topical antibiotics of different chemical nature. The murine model used consisted of surgical wounds infected with *S. aureus* or *S. pyogenes*. The topical treatment was applied 4 and 10 hours post-infection and the treatment with systemic antibiotics at clinically relevant doses was administered 4, 8 and 12 hours post-infection; both treatments were continued 3 times/day for 3 days.

Among the results it was reported that mupirocin cream was statistically ($p<0.01$) more effective than mupirocin ointment in reducing the number of bacteria present in the wounds. Mupirocin cream was similar in efficacy to flucloxacillin but statistically more effective ($p<0.001$) than oral erythromycin. It also showed similar efficacy to cefalexine vs *S. pyogenes* but higher against *S. aureus* ($p<0.01$). Mupirocin cream showed the same efficacy as fusidic acid against *S. aureus* but significantly higher against *S. pyogenes* ($p<0.01$).

An impetigo murine model infected with *S. aureus* was also used in this study. The treatments used included topical and systemic antibiotics within 24 and 30 hours post-infection (as well as 36 hours post-infection for oral antibiotics) and subsequently 3 times/day for 2 days more. At the fifth day of treatment mupirocin cream was statistically more effective than mupirocin ointment ($p<0.01$) and erythromycin and cefalexine. With these data the efficacy of mupirocin cream as topical antibiotic is proven in the use of bacterial skin infections such as impetigo. With this, the involvement of betamethasone dipropionate in the efficiency, safety and absorption ability to the action site is demonstrated.

Hydrogenated castor oil is used as a cosolvent for enhancing solubility of mupirocin. Further, at the concentration used in the formula, it confers mildness to the product. This material when used as an excipient for products intended to be topically applied, is relatively non toxic and non irritant such that its safeness is demonstrated in this way.

PEG 150 distearate is used as thickener agent which, by being a polyethylene glycol, shows affinity both for PEG 40 hidrogenated castor oil and polyethylene glycol 600, so there is no interaction or incompatibility of any kind with the rest of the product excipients. This material when used as excipient for products intended to be topically applied, is relatively non toxic and non irritant so its safeness is thus demonstrated.

Polyethylene glycol 600 is used as a carrier that, by being a polyethylene glycol, shows affinity both for PEG hydrogenated castor oil and PEG 150 distearate so there is no is no interaction or incompatibility of any kind with the rest of the product excipients. This material when used as excipient for products intended to be topically applied, is relatively non toxic and non irritant so its safeness is thus demonstrated.

For a better understanding of the invention, it follows a detailed description of one its embodiments, shown in the examples that for illustrative but not limitative purposes are attached to the present disclosure.

DETAILED DISCLOSURE OF THE INVENTION

The present preparation is a product having a broad antibacterial spectrum, with anti-inflammatory and antipruritic activity. It is a formulation that can be made by using a manufacturing process which assures the highest product quality as a result of controls that take place during manufacturing and conditioning processes with a formula that fulfills stability standards, wherein each and every ingredient is in balance.

Due to the antibacterial and anti-inflammatory residual action of the combination of actives, the composition offers a protection protracted action even after 24 hours of application provided that the product has not been intentionally or incidentally removed. This allows to consider that with the constant use of the present invention composition, a higher therapeutic efficacy is obtained than if the products were used including the actives separately.

In the tests conducted on the product suitable composition, it could be established that if mupirocin concentration is substantially reduced to less than 2.0% the efficacy of the product is reduced, thus delaying the therapeutic activity of the product by lengthening treatment time. Further, it could be confirmed that if the active concentration is substantially increased over 5%, even when all the active is absorbed there are no toxic effects or in very few occasions the product can cause pruritus and erythema on the patient which disappear when suspending the medicament. There are no data which demonstrate an increase in the product's efficiency or efficacy.

As regards to betamethasone dipropionate, it could be established that if the concentration is substantially reduced from 0.0500% the efficacy of the product is reduced, thus delaying the therapeutic activity of the product by lengthening treatment time and in the worst case, no active absorption will be achieved and the therapeutic activity shall be null. If the active concentration is substantially increased over 0.0643%, excessive and protracted use of topical corticosteroids could suppress pituitary-suprarenal function, thus causing secondary suprarenal failure with manifestations of hypercorticism, including Cushing's syndrome and in few occasions the product could cause in the patient a feeling of burning, itching, irritation, dryness, folliculitis, hypertrichosis, acneiform eruptions, hypopigmentation, perioral dermatitis, allergic contact dermatitis, skin maceration, secondary infection, skin atrophy, striae and miliaria, which disappear by gradually suspending the medicament. There are no data which demonstrate an increase in the product's efficiency or efficacy.

The product further has three excipients, one for attaining dissolution of the molecule active components, other giving the product viscosity and the other being the balance carrier. These excipients are specific to achieve above all stability of the product. No other dissolvent, nor no other viscosity modifier, as well as no other carrier, achieve stability of the active compounds.

As dissolvent use is made of PEG 40 hydrogenated castor oil. If the concentration is substantially reduced under 5.00% the carrier dissolution ability for solving mupirocin is reduced. If the excipient concentration is substantially increased over 15.0%, the product is made more expensive and PEG 40 hydrogenated castor oil function starts to modify the product's physical characteristics rendering it harder and difficult to apply.

As viscosity modification agent use is made of PEG 150 distearate. If the concentration is substantially reduced under 10.0% the product loses viscosity thus making it too fluid and also losing its functionality and rendering its handling cumbersome by being conditioned in aluminum tube as primary container. If the excipient concentration is substantially increased over 20.0%, viscosity shall be increased to such an extent that its conditioning in the primary container, the handling thereof and its functionality shall be highly affected until making it even more difficult to apply and unpleasant for the patient.

Finally, the chosen carrier is polyethylene glycol 600. As this excipient is the balance carrier, if concentrations of the remainder of the formula excipients are observed, the result of the product application shall not be altered if used under 40.0% and above 80.0%.

For determining this standard levels, a series of tests discussed in the following examples were performed.

EXAMPLES

Example 1

Room Temperature Solubilities

TABLE 1

Solubility tests for product actives by mixing at 60 rpm and at room temperature

| Condition | Solvent | Mupirocin | Betamethasone dipropionate |
|---|---|---|---|
| Room temperature Constant Mixing | Purified Water | + | + |
| | Propyleneglycol | + | + |
| | Polyethylene glycol 600 | + | + |
| | Glycerin | + | + |
| | PEG 40 Hydrogenated castor oil | ++ | ++ |
| | Mineral oil | + | + |

(+ = Insoluble; ++ = mildly soluble; +++ = soluble; ++++ = very soluble)

Example 2

Solubilities at 60° C.

TABLE 2

Solubility tests for product actives by mixing at 60 rpm and 60° C. temperature

| Condition | Solvent | Mupirocin | Betamethasone dipropionate |
|---|---|---|---|
| Room temperature Constant Mixing | Purified Water | + | + |
| | Propyleneglycol | ++ | ++++ |
| | Polyethylene glycol 600 | +++ | ++++ |
| | Glycerin | ++ | +++ |
| | PEG 40 Hydrogenated castor oil | ++++ | ++++ |
| | Mineral oil | ++ | ++++ |

(+ = Insoluble; ++ = mildly soluble; +++ = soluble; ++++ = very soluble)

From the solubility tests reported in Table No. 1 and 2, it is concluded that the most suitable solvent for dissolving mupirocin and betamethasone dipropionate is PEG 40 hydrogenated castor oil and the condition for achieving their dissolution is by heating the solvent to 60° C.

As for the ointment base determination, an ointment base having the following components was tested: white petrolatum (carrier), NF 85 mineral oil (texture and appearance modifier), PEG 40 hydrogenated castor oil (solvent), glycerin (moistener), butyl hydroxy toluene (antioxidant), methyl paraben and propyl paraben (preservatives), mupirocin and betamethasone dipropionate (active ingredients). The manufacture process was the following: In an appropriate size vessel the white petrolatum, mineral oil and glycerin were placed, this mixture was heated up to a temperature of 75° C. and then the butyl hydroxy toluene with the parabens was dissolved; separately in other suitable size vessel the PEG 40 hydrogenated castor oil was placed, heated up to a 60° C. temperature and mupirocin and betamethasone dipropionate were solved therein; when both mixtures were at 60° C. they were mixed and the final product was obtained after lowering the temperature with constant mixing until reaching ambient temperature.

Once the product was obtained three samples were analyzed, collected from different parts of the vessel containing the product, by Active Evaluation techniques reported for each of them in the individual monographs included in USP23 NF/21. Results are reported in Table No. 3.

TABLE 3

Results obtained after evaluating the actives for the proposed formula

| Active Principle | | Evaluation | |
|---|---|---|---|
| | | Results (%) | Specification |
| Mupirocin | Sample 1 | 70.5 | 90.0 to 110.0% |
| | Sample 2 | 71.2 | |
| | Sample 3 | 70.7 | |
| Betamethasone dipropionate | Sample 1 | 100.6 | 90.0 to 110.0% |
| | Sample 2 | 100.2 | |
| | Sample 3 | 100.2 | |

The above results indicate that the product is homogeneous because of the uniformity of the obtained results, but it is assumed that mupirocin has some incompatibility with some of the excipients because its evaluation is practically 30% under the expected mean.

In order to test the possible incompatibility of mupirocin with one of the excipients the following tests reported in Table No. 4 were performed and the results are the following:

TABLE 4

Incompatibility tests and evaluation results when analyzing the product immediately after being prepared

| | TESTS | | | | | | |
|---|---|---|---|---|---|---|---|
| INGREDIENTS | 1 | 2 | 3 | 4 | 5 | 6 | 7 |
| Mupirocin | x | x | x | x | x | x | x |
| Betamethasone dip. | x | x | x | x | x | x | x |
| PEG 40 hydrogenated castor oil | x | x | x | x | x | x | x |
| Butyl hydroxy toluene | — | x | x | x | x | x | x |
| Propyl paraben | — | — | x | x | x | x | x |
| Methyl paraben | — | — | — | x | x | x | x |
| Glycerin | — | — | — | — | x | x | x |
| Mineral oil | — | — | — | — | — | x | x |
| White petrolatum | — | — | — | — | — | — | x |
| Mupirocin evaluation | 98.8 | 99.3 | 98.7 | 98.9 | 99.0 | 98.8 | 69.8 |
| Betamethasone dip. evaluation | 100.2 | 100.3 | 100.2 | 99.8 | 100.2 | 100.4 | 99.3 |

According to the results it can be concluded that mupirocin in the presence of white petrolatum undergoes a possible chemical degrading. It then followed a simple incorporation of the active in the white petrolatum at a temperature of 60° C. and it was seen that immediately a cream color precipitate forms having a gummy appearance and hard. With these data it can be concluded that mupirocin is incompatible with white petrolatum. Therefore, this ointment base with mupirocin is discarded.

From the up to now obtained results, other ointment base wherein there is any kind of petrolatum or any petroleum-derived hydrocarbon is proposed.

Taking the experience that mupirocin and betamethasone dipropionate are soluble at 60° C. in PEG 40 hydrogenated castor oil and in polyethylene glycol 600 (according to Table No. 2), a formulation having the following ingredients is proposed: mupirocin and betamethasone dipropionate (active ingredients), PEG 40 hydrogenated castor oil (cosolvent), polyethylene glycol 600 (balance excipient or carrier), PEG 150 distearate (thickener) and methyl paraben (preservative). The manufacturing process was the following: In an appropriate size vessel the polyethylene glycol 600 and PEG 40 hydrogenated castor oil were placed, this mixture was heated up to a temperature of 70° C. and then the methyl paraben, mupirocin and betamethasone dipropionate were dissolved; once all the above ingredients were dissolved, the temperature was lowered with constant mixing until reaching 60° C.; it was then added the PEG 150 distearate and continued mixing until the mixture was homogenous; the final product was obtained after lowering the temperature with constant mixing until reaching ambient temperature.

Once the product was obtained three samples were analyzed, collected from different parts of the vessel containing the product, by Active Evaluation techniques reported for each of them in the individual monographs included in USP23 NF/21. Results are reported in Table No. 5.

TABLE 5

Results obtained after evaluating the actives for the proposed formula

| Active Principle | | Evaluation | |
|---|---|---|---|
| | | Results (%) | Specification |
| Mupirocin | Sample 1 | 98.7 | 90.0 to 110.0% |
| | Sample 2 | 99.1 | |
| | Sample 3 | 99.4 | |
| Betamethasone dipropionate | Sample 1 | 99.8 | 90.0 to 110.0% |
| | Sample 2 | 100.3 | |
| | Sample 3 | 100.1 | |

The product also has physical properties with suitable features for the ointment pharmaceutical form (Appearance: an homogeneous, spreadable white color semi-solid free from foreign particles and with a characteristic odor; pH 7.5; viscosity 80,000 cPs).

Finally, with the results obtained in Table No. 5, the obtained formulation was subject to the accelerated stability test according to Mexican Official Standard NOM-073-SSA1-1993, Medicament Stability. The results obtained after the three-month period of testing were satisfactory.

After these tests and some other more the following composition possibilities of the product object of the present disclosure were obtained.

TABLE 7

Ingredients and their concentrations to be protected by the present patent

| Ingredient | Function |
| --- | --- |
| Mupirocin | Active |
| Betamethasone dipropionate | Active |
| PEG 40 hydrogenated castor oil and any derivative or combination of hydrogenated castor oil | Cosolvent |
| PEG 150 distearate and any derivative or combination of polyethylene glycols | Thickener |
| Polyethylene glycol 600 and any derivative or combination of polyethylene glycols | Carrier |
| Methyl paraben and its salts, ethyl paraben and its salts, propyl paraben and its salts, butyl paraben and its salts, butyl hydroxy anisole, bentonite, imidazolidinyl urea, potassium metabisulphite, potassium sorbate, propionic acid, propyl gallate, sodium benzoate, sodium metabisulphite, sodium propionate, thimerosal, xylitol. | Preservative |

The invention has been sufficiently disclosed for a person skilled in the art to reproduce and achieve the same results as those mentioned in the present invention. However, any person having an average skill in the field to which the present invention belongs can be able of making modifications not disclosed in the present application, however, if for the application of these modifications to a determined composition or in the manufacturing process thereof, the subject matter claimed in the following claims is needed, said structures must be comprised within the scope of the invention.

The invention claimed is:

1. A topical formulation containing mupirocin and betamethasone dipropionate, PEG 40 hydrogenated castor oil, PEG 150 distearate, polyethylene glycol 600, and optionally one or more preservatives.

2. Skin-care preparations containing mupirocin and betamethasone dipropionate, characterized by having the following quantitative composition:

| Ingredient | Composition content |
| --- | --- |
| Mupirocin | 2.0%-5.0% |
| Betamethasone dipropionate | 0.05%-0.06% |
| hydrogenated castor oil | 5.0%-15.0% |
| PEG 150 distearate | 10.0%-20.0% |
| Polyethylene glycol 600 | 40.0%-80.0%. |

3. The formulation according to claim 1 wherein the mupirocin is present in an amount of 2.0 to 5.0% w/w.

4. The formulation according to claim 1 wherein the betamethasone dipropionate is present in an amount of 0.05%-0.064% w/w.

5. The formulation according to claim 1 wherein the Hydrogenated castor oil is present in an amount of 5.0%-15.0% w/w.

6. The formulation according to claim 1 wherein the PEG 150 distearate is present in an amount of 10.0%-20.0% w/w.

7. The formulation according to claim 1 wherein the Polyethylene glycol 600 is present in an amount of 40.0%-80.0% w/w.

* * * * *